United States Patent [19]

Caplan et al.

[11] Patent Number: 5,197,985

[45] Date of Patent: Mar. 30, 1993

[54] METHOD FOR ENHANCING THE IMPLANTATION AND DIFFERENTIATION OF MARROW-DERIVED MESENCHYMAL CELLS

[76] Inventors: Arnold I. Caplan, 1300 Oakridge Dr., Cleveland Heights, Ohio 44121; Stephen E. Haynesworth, 3643 Antisdale Rd., Cleveland Heights, Ohio 44118

[21] Appl. No.: 614,915

[22] Filed: Nov. 16, 1990

[51] Int. Cl.⁵ .......................... A61F 2/28; A61K 35/12
[52] U.S. Cl. .......................................... 623/16; 623/11; 623/66; 530/838; 530/840
[58] Field of Search .............. 623/16, 11, 12, 66, 623/18; 424/95; 530/838, 840; 514/2

[56] References Cited

U.S. PATENT DOCUMENTS

| | | | |
|---|---|---|---|
| 3,968,567 | 7/1976 | Nevins | 623/66 |
| 4,430,760 | 2/1984 | Smestad | 623/16 |
| 4,596,574 | 6/1986 | Urist | 623/16 |
| 4,609,551 | 9/1986 | Caplan et al. | 623/16 |
| 4,642,120 | 2/1987 | Nevo et al. | 623/16 |
| 4,846,835 | 7/1989 | Grande | 623/16 |
| 4,904,259 | 2/1990 | Itay | 623/66 |
| 5,011,495 | 4/1991 | Hollinger | 623/16 |
| 5,061,286 | 10/1991 | Lyle | 623/66 |

*Primary Examiner*—Randall L. Green
*Assistant Examiner*—Debra S. Brittingham
*Attorney, Agent, or Firm*—Fay, Sharpe, Beall, Fagan, Minnich & McKee

[57] ABSTRACT

The present invention is directed to a method and device for enhancing the implantation and differentiation of marrow-derived mesenchymal cells (i.e. mesenchymal stem cells). The method and device of the invention are an effective means for treating skeletal and other connective tissue disorders.

15 Claims, 4 Drawing Sheets

METHOD FOR ENHANCING THE IMPLANTATION AND DIFFERENTIATION OF MARROW-DERIVED MESENCHYMAL CELLS

BACKGROUND OF THE INVENTION

The present invention is directed to various methods and devices for enhancing the implantation and differentiation of marrow-derived mesenchymal cells (i.e. mesenchymal stem cells).

Marrow-derived mesenchymal cells are the formative pluripotential blast cells found in the bone that are believed to be capable of differentiating into any of the specific types of connective tissues (i.e. the tissues of the body that support the specialized elements; particularly adipose, areolar, osseous, cartilaginous, elastic, and fibrous connective tissues) depending upon various environmental influences. Although these cells are normally present at very low frequencies in bone marrow, the inventors of the present invention have discovered a process for isolating, purifying, and greatly replicating the marrow-derived mesenchymal cells in culture, i.e. in vitro. This discovery is the subject of a co-pending U.S. patent application.

The present invention is directed to various devices and factors which have been developed in order to induce the culturally expanded marrow-derived mesenchymal cells to differentiate into specific types of desired phenotypes, such as bone or cartilage forming cells. For example, the inventors have found that various porous tri-calcium or hydroxyaptite ceramic devices can be utilized as vehicles or carriers for the culturally expanded marrow-derived mesenchymal cells when implanted into skeletal defects thereby permitting and/or promoting the differentiation of the cells into skeletal tissue.

Along this line, the inventors have discovered that certain factors, such as mechanical, cellular, and biochemical stimuli can be utilized in order to induce differentiation of the culturally expanded marrow-derived mesenchymal cells into bone forming cells, etc. Thus, the present invention provides for methods of utilizing the culturally expanded marrow-derived mesenchymal cells for correcting or modifying connective tissue disorders, such as the regeneration of missing or damaged skeletal tissue, enhancing the implantation of various plastic or metal prosthetic devices, etc., through the incorporation of the isolated and culturally expanded marrow-derived mesenchymal cells onto the porous surfaces of various tri-calcium or hydroxyaptite ceramic vehicles or carriers. Upon the activation and subsequent differentiation of the marrow-derived mesenchymal cells present in the porous ceramic vehicles or carriers, new connective tissues, such as natural viscous bridges, etc., can be generated.

SUMMARY OF THE INVENTION

The present invention relates to a method and device for enhancing the implantation and differentiation of marrow-derived mesenchymal cells. The method comprises the steps of providing culturally expanded purified marrow-derived mesenchymal cells, and applying the culturally expanded purified marrow-derived mesenchymal cells to a desired area of connective tissue regeneration, such as an area of connective tissue damage, by means of a vehicle or carrier, under conditions suitable for differentiating the cells present in the carrier into the type of connective tissue desired, such as the type of connective tissue necessary for repair. A device for repairing connective tissue damage comprising of a carrier containing culturally expanded marrow-derived mesenchymal cells is also provided.

More particularly, one embodiment of the invention is directed to a method for using a porous ceramic composition comprised of tri-calcium phosphate or hydroxyapatite or combinations of the two, as a vehicle or carrier for marrow-derived mesenchymal cells, which, when implanted into skeletal defects, promotes the differentiation of the cells into skeletal tissue.

In a further aspect, the present invention is directed to a method for repairing skeletal defects. The method comprises the steps of providing a bone marrow specimen containing marrow-derived mesenchymal cells, adding cells from the bone marrow specimen to a medium (i.e. "complete medium") which contains factors that stimulate marrow-derived mesenchymal cell growth without differentiation and allows, when cultured, for the selective adherence of only the marrow-derived mesenchymal cells to a substrate surface, culturing the bone marrow-medium mixture, removing the non-adherent matter from the substrate surface by replacing the medium with a fresh medium of the same composition, and, allowing the isolated adherent marrow-derived mesenchymal cells to culturally expand. The culturally expanded marrow-derived mesenchymal cells are then applied to a porous carrier, such as a porous calcium phosphate and/or hydroxyapatite ceramic block, which is subsequently implanted into the defective skeletal tissue. It has been found that through the use of the porous carrier containing the culturally expanded mesenchymal cells, the mesenchymal cells fairly rapidly differentiate into bone producing cells. As a result, the method and device of the invention are an effective means for treating skeletal and other connective tissue disorders.

DESCRIPTION OF THE DRAWINGS

The following is a brief description of the drawings which are presented for the purposes of illustrating the invention and not for the purposes of limiting the same.

FIG. 2 is a series of photomicrographs (Mallory Heidehain Staining) of a histological section of a composite containing cultured human marrow fibroblasts and ceramic after two weeks of incubation in a nude mouse.

FIG. 3 is a series of photomicrographs (Mallory Heidehian staining) of a histological section of a composite containing cultured human marrow fibroblasts in ceramic after three weeks of incubation in a nude mouse.

FIG. 4 is two photomicrographs (Mallory Heidenhain staining) of a histological section of cultured human marrow fibroblasts in ceramic after six weeks of incubation in a nude mouse.

DETAILED DESCRIPTION OF THE INVENTION

Figure 1:
FIG. 1 is a phase contrast photomicrograph of a monolayer culture of fibroblast-like cells derived from human marrow (100×)

The present invention is derived from the discovery that through a fairly detailed process, the progenitor cells to the various types of connective tissues can be isolated and purified from tissue such as bone marrow. These cells are referred to as "marrow-derived mesenchymal cells" by the present inventors. In this regard, it has been found that although the progenitor marrow-derived mesenchymal cells (i.e. the mesenchymal stem cells) are normally present in bone marrow in very minute amounts and that these amounts greatly decrease with age (i.e. from about 1/10,000 cells in a relatively young patient to about 1/1,000,000 in an elderly patient), the progenitor cells (i.e. the marrow-derived mesenchymal cells or mesenchymal stem cells) can be isolated from tissue and purified when cultured in a specific medium by their selective attachment to substrates. As indicated above, this discovery is the subject matter of a co-pending U.S. patent application.

Furthermore, it has also been found that the isolated and purified marrow-derived mesenchymal cells can be grown in an undifferentiated state through mitotic expansion in a specific medium. These cells can then be harvested and activated to differentiate into bone, cartilage, and various other types of connective tissue by a number of factors, including mechanical, cellular, and biochemical stimuli. As a result, it has been determined that the marrow-derived mesenchymal cells possess the potential to differentiate into cells which produce various types of connective tissue, such as osteoblasts and chondrocytes, and possibly tendon, ligament and dermis, and that this potential is retained after isolation and for several population expansions in culture. Thus, by being able to isolate, purify, greatly multiply, and then activate the marrow-derived mesenchymal cells to differentiate into the specific types of connective tissue desired, such as bone-forming osteoblast cells, etc., a highly effective process exists for treating skeletal and other connective tissue disorders.

In this regard, the present inventors have discovered that when the culturally-expanded mesenchymal cells are loaded into various porous carrier vehicles under certain conditions, the culturally-expanded mesenchymal cells have the ability to differentiate into bone-forming osteoblast cells, as opposed to cartilage forming cells. As a result, the isolated and culturally expanded marrow-derived mesenchymal cells can be utilized in certain porous vehicles or carriers, to produce the desired phenotype needed for connective tissue repair and/or the implantation of various prosthestic devices. This discovery is the subject of the present application.

More particularly, bone marrow is the soft tissue occupying the medullary cavities of long bones, some haversian canals, and spaces between trabecular of cancellous or spongy bone. Bone marrow is of two types—red, which is found in all bones in early life and in restricted locations in adulthood (i.e. in the spongy bone) and is concerned with the production of blood cells (i.e. hemopoiesis) and hemoglobin (thus, the red color); and yellow, which consists largely of fat cells (thus, the yellow color) and connective tissue.

As a whole, bone marrow is a complex tissue comprised of red and white blood cells, their precursors, and a group of cells consisting of fibroblasts, reticulocytes, adipocytes, and endothelial cells which formulate a connective tissue network called "stroma". Cells from the stroma morphologically regulate the differentiation of hemopoietic cells through direct interaction via cell surface proteins and the secretion of growth factors and are involved in the foundation and support of the bone structure. Studies using animal models have suggested that bone marrow contains "prestromal" cells which have the capacity to differentiate into cartilage, bone, and other connective tissue cells. (Beresford, J. N.: Osteogenic Stem Cells and the Stromal System of Bone and Marrow, *Clin. Orthop.*, 240:270, 1989). Recent evidence indicates that these cells, called pluripotent stromal stem cells or mesenchymal stem cells, have the ability to generate into several different types of cell lines (i.e. osteocytes, chondocytes, adipocytes, etc.) upon activation. However, the mesenchymal stem cells are present in the tissue not only in very minute amounts with a wide variety of other cells (i.e. erythrocytes, platelets, neutrophils, lymphocytes, monocytes, cosimophils, basophils, adipose cells, etc.) in an inverse relationship with age, they are capable of differentiating into an assortment of connective tissues depending upon the influence of a number of bioactive factors.

As a result, one aspect of the present invention is directed to a process of isolating and purifying the marrow-derived mesenchymal cells from tissue prior to differentiation and then culturally expanding the marrow-derived mesenchymal cells to produce a valuable tool for skeletal therapy. The objective of such manipulation is to greatly increase the number of potentially reparative cells and to utilize these cells to redirect and/or reinforce the body's normal reparative capacity. In this regard, the marrow-derived mesenchymal cells can then be subsequently harvested in great numbers and applied to areas of connective tissue damage through the use of various porous ceramic vehicles in order to enhance or stimulate in-vivo growth for regeneration and/or repair, to improve implant adhesion to various prosthetic devices through subsequent activation and differentiation, enhance hemopoietic cell production, etc.

Along these lines, various procedures are contemplated by the inventors for transferring, immobilizing, and activating the culturally expanded, purified marrow-derived mesenchymal cells at the site for repair, implantation, etc., through the use of various porous ceramic vehicles or carriers, including injecting the cells into the porous ceramic vehicle or carrier at the site of a skeletal defect, incubating the cells with the porous ceramic vehicle or carrier attached to a prosthesis and implanting the carrier-prosthesis device, etc. Thus, by isolating, purifying and greatly expanding the number of cells prior to differentiation and then actively controlling the differentiation process through the use of various vehicles or carriers, the culturally expanded undifferentiated marrow-derived mesenchymal cells can be utilized for various therapeutic purposes such as to elucidate cellular, molecular, and genetic disorders in a wide number of metabolic bone diseases and skeletal dysplasias.

As more specifically indicated below in Example 1, the marrow-derived mesenchymal cells isolated and purified in the present invention were derived from bone marrow attained from a number of different sources, including plugs in femoral head cancellous bone pieces obtained from patients with degenerative joint disease during hip or knee replacement surgery, and from aspirated marrow obtained from normal donors and oncology patients who have marrow harvested for future bone marrow transplatation. Although the harvested marrow was prepared for cell culture separation by a number of different mechanical isolation processes depending upon the source of the harvested marrow (i.e. the presence of bone chips, peripheral blood etc.), the critical step involved in the isolation processes was the use of a specially prepared medium which contained agents which allowed for not only marrow-derived mesenchymal cell growth without differentiation but also for the direct adherence of only the marrow-derived mesenchymal cells to the plastic or glass surface area of the culture dish. By producing a medium which allowed for the selective attachment of the desired marrow-derived mesenchymal cells which were present in the marrow samples in very minute amounts, it was possible to separate the mesenchymal stem cells from the other cells (i.e. red and white blood cells, etc.) present in the bone marrow.

In this regard, it was found that a medium consisting of BGJ$_b$ medium (Gibco, Grand Island, N.Y.) with tested and selected lots of 10% fetal bovine serum (J. R. Scientific, Woodland, Calif., or other suppliers) was well suited for use in the present invention. This medium, which was called "complete medium", contained factors which stimulated marrow-derived mesenchymal cell growth without differentiation and allowed for the selective attachment through specific protein binding sites, etc. of only the marrow-derived mesenchymal cells to the plastic surfaces of Petri dishes. Although the specific operating mechanism of the complete medium for producing the differential attachment is currently not well understood, research is continuing in this area.

The principal components of the BGJ$_b$ Medium (Fitton-Jackson Modification) utilized to formulate the complete medium are set forth below:

| BGJ$_b$ Medium (Fitton-Jackson Modification) | |
|---|---|
| Liquid Component | 320-2591  1X (mg/L) |
| Inorganic Salts: | |
| NaH$_2$PO$_4$.H$_2$O | 90.00 |
| MgSO$_4$.7H$_2$O | 200.00 |
| KCl | 400.00 |
| KH$_2$PO$_4$ | 160.00 |
| NaHCO$_3$ | 3500.00 |
| NaCl | 5300.00 |
| Other Components: | |
| Calcium Lactate | 550.00 |
| D-Glucose | 10000.00 |
| Phenol red | 20.00 |
| Sodium acetate | 50.00 |
| Amino Acids: | |
| L-Alanine | 250.00 |
| L-Arginine | 175.00 |
| L-Arginine HCl | — |
| L-Aspartic acid | 150.00 |
| L-Cysteine HCl.H$_2$O | 101.00 |
| L-Glutamine | 200.00 |

-continued

| BGJ$_b$ Medium (Fitton-Jackson Modification) | |
|---|---|
| Liquid Component | 320-2591  1X (mg/L) |
| Glycine | 800.00 |
| L-Histidine | 150.00 |
| L-Histidine HCl.H$_2$O | — |
| L-Isoleucine | 30.00 |
| L-Leucine | 50.00 |
| L-Lysine | 240.00 |
| L-Lysine HCl | — |
| L-Methionine | 50.00 |
| L-Phenylalanine | 50.00 |
| L-Proline | 400.00 |
| L-Serine | 200.00 |
| L-Threonine | 75.00 |
| L-Tryptophan | 40.00 |
| L-Tyrosine | 40.00 |
| DL-Valine | 65.00 |
| L-Valine | — |
| Vitamins: | |
| α-tocopherol phosphate (disodium salt) | 1.00 |
| Ascorbic acid | 50.00 |
| Biotin | 0.20 |
| D-Ca pantothenate | 0.20 |
| Choline chloride | 50.00 |
| Folic acid | 0.20 |
| i-Inositol | 0.20 |
| Nicotinamide | 20.00 |
| Para-aminobenzoic acid | 2.00 |
| Pyridoxal phosphate | 0.20 |
| Riboflavin | 0.20 |
| Thiamine HCl | 4.00 |
| Vitamin B$_{12}$ | 0.04 |

In addition, it was also found that the medium F-12 Nutrient Mixture (Ham) (Gibco, Grand Island, N.Y.) exhibited the desired properties for selective marrow-derived mesenchymal cell separation. The principal components of the F-12 Nutrient Mixture (Ham) are as follows:

| F-12 Nutrient Mixture (Ham) | | |
|---|---|---|
| Component | 320-1765 1X Liquid (mg/L) | 430-1700 Powder (mg/L) |
| Inorganic Salts: | | |
| CaCl$_2$ (anhyd.) | — | 33.22 |
| CaCl$_2$.2H$_2$O | 44.00 | — |
| CuSO$_4$.5H$_2$O | 0.00249 | 0.00249 |
| FeSO$_4$.7H$_2$O | 0.834 | 0.834 |
| KCl | 223.60 | 223.60 |
| KH$_2$PO$_4$ | — | — |
| MgCl$_2$ (anhyd.) | — | 57.22 |
| MgCl$_2$.6H$_2$O | 122.00 | — |
| MgSO$_4$ (anhyd.) | — | — |
| MgSo$_4$.7H$_2$O | — | — |
| NaCl | 7599.00 | 7599.00 |
| NaHCO$_3$ | 1176.00 | — |
| Na$_2$HPO$_4$ (anhyd.) | — | 142.04 |
| Na$_2$HPO$_4$.7H$_2$O | 268.00 | — |
| ZnSO$_4$.7H$_2$O | 0.863 | 0.863 |
| Other Components: | | |
| D-Glucose | 1802.00 | 1802.00 |
| Hypoxanthine | 4.10 | — |
| Hypoxanthine (sodium salt) | — | 4.77 |
| Linoleic acid | 0.084 | 0.084 |
| Lipoic acid | 0.21 | 0.21 |
| Phenol red | 1.20 | 1.20 |
| Putrescine 2HCl | 0.161 | 0.161 |
| Sodium pyruvate | 110.00 | 110.00 |
| Thymidine | 0.73 | 0.73 |
| Amino Acids: | | |
| L-Alanine | 8.90 | 8.90 |
| L-Arginine HCl | 211.00 | 211.00 |
| L-Asparagine.H$_2$O | 15.01 | 15.01 |
| L-Aspartic acid | 13.30 | 13.30 |

-continued

| F-12 Nutrient Mixture (Ham) | | |
|---|---|---|
| Component | 320-1765 1X Liquid (mg/L) | 430-1700 Powder (mg/L) |
| L-Cysteine | — | — |
| L-Cysteine HCl.H$_2$O | 35.12 | 35.12 |
| L-Glutamic acid | 14.70 | 14.70 |
| L-Glutamine | 146.00 | 146.00 |
| Glycine | 7.50 | 7.50 |
| L-Histidine HCl.H$_2$O | 20.96 | 20.96 |
| L-Isoleucine | 3.94 | 3.94 |
| L-Leucine | 13.10 | 13.10 |
| L-Lysine HCl | 36.50 | 36.50 |
| L-Methionine | 4.48 | 4.48 |
| L-Phenylalanine | 4.96 | 4.96 |
| L-Proline | 34.50 | 34.50 |
| L-Serine | 10.50 | 10.50 |
| L-Threonine | 11.90 | 11.90 |
| L-Tryptophan | 2.04 | 2.04 |
| L-Tyrosine | 5.40 | — |
| L-Tyrosine (disodium salt) | — | 7.78 |
| L-Valine | 11.70 | 11.70 |

As indicated above, the complete medium can be utilized in a number of different isolation processes depending upon the specific type of initial harvesting processes used in order to prepare the harvested bone marrow for cell culture separation. In this regard, when plugs of cancellous bone marrow were utilized, the marrow was added to the complete medium and vortexed to form a dispersion which was then centrifuged to separate the marrow cells from bone pieces, etc. The marrow cells (consisting predominantly of red and white blood cells, and a very minute amount of mesenchymal stem cells, etc.) were then dissociated into single cells by passing the complete medium containing the marrow cells through syringes fitted with a series of 16, 18, and 20 gauge needles. It is believed that the advantage produced through the utilization of the mechanical separation process, as opposed to any enzymatic separation process, was that the mechanical process produced little cellular change while an enzymatic process could produce cellular damage particularly to the protein binding sites needed for culture adherence and selective separation, and/or to the protein sites needed for the production of monoclonal antibodies specific for said marrow-derived mesenchymal cells. The single cell suspension (which was made up of approximately 50–100×10$^6$ nucleated cells) was then subsequently plated in 100 mm dishes for the purpose of selectively separating and/or isolating the marrow-derived mesenchymal cells from the remaining cells found in the suspension.

When aspirated marrow was utilized as the source of the marrow-derived mesenchymal cells, the marrow stem cells (which contained little or no bone chips but a great deal of blood) were added to the complete medium and fractionated with Percoll (Sigma, St. Louis, Mo.) gradients more particularly described below in Example 1. The Percoll gradients separated a large percentage of the red blood cells and the mononucleate hemopoietic cells from the low density platelet fraction which contained the marrow-derived mesenchymal stem cells. In this regard, the platelet fraction, which contained approximately 30–50×10$^6$ cells was made up of an undetermined amount of platelet cells, 30–50×10$^6$ nucleated cells, and only about 50–500 marrow-derived mesenchymal cells depending upon the age of the marrow donor. The low density platelet fraction was then plated in the Petri dish for selective separation based upon cell adherence.

In this regard, the marrow cells obtained from either the cancellous bone or iliac aspirate (i.e. the primary cultures) were grown in complete medium and allowed to adhere to the surface of the Petri dishes for one to seven days according to the conditions set forth in Example 1 below. Since no increase in cell attachment was observed after the third day, three days was chosen as the standard length of time at which the non-adherent cells were removed from the cultures by replacing the original complete medium with fresh complete medium. Subsequent medium changes were performed every four days until the culture dishes became confluent which normally required 14–21 days. This represented 10$^3$–10$^4$ fold increase in undifferentiated mesenchymal stem cells.

The cells were then detached from the culture dishes utilizing a releasing agent such as trypsin with EDTA (ethylene diaminetetra-acetic acid) (0.25% trysin, 1 mM EDTA (1X), Gibco, Grand Island, N.Y.) or a chelating agent such as EGTA (ethylene glycol-bis-(2-amino ethyl ether) N,N'-tetraacetic acid, Sigma Chemical Co., St. Louis, Mo.). The advantage produced through the use of a chelating agent over trypsin was than trypsin could possibly cleave off a number of the binding proteins of the mesenchymal stem cells. Since these binding proteins contain recognition sites, when monoclonal antibodies were sought to be produced, a chelating agent such as EGTA as opposed to trypsin, was utilized as the releasing agent. The releasing agent was then inactivated and the detached cultured undifferentiated stem cells were washed with complete medium for subsequent use.

In this regard, the bone and cartilage lineage potentials (i.e. osteo-chondrogenic potential) of fresh and expanded marrow-derived mesenchymal cells under the influence of various bioactive factors were determined using two different in-vivo assays in nude mice. See Example 1 below. One assay involved the subcutaneous implantation of porous calcium phosphate and/or hydroxyapatite ceramics loaded with cultured marrow-derived mesenchymal cells; the other involved peritoneal implantation of diffusion chambers inoculated with cultured marrow-derived mesenchymal cells. Whole marrow and Percoll gradient separated aspirate fractions were also analyzed in these in-vivo assays. Histological evaluation showed bone formation in the ceramics implanted with the cultured mesenchymal stem cells derived from the femoral head and the iliac crest. No cartilage was observed in any of the ceramic grafts. In contrast, the same cells failed to form any bone or cartilage in the diffusion chambers. While whole marrow has now been shown to form bone when placed as a composite graft with ceramics in a subcutaneous site in nude mice, the amount of bone produced is substantially less than that seen when culture-expanded marrow-derived mesenchymal cells are used.

These results indicated that under certain conditions, culturally expanded mesenchymal cells have the ability to differentiate into bone when incubated as a graft in a porous calcium phosphate and/or hydroxyapatite ceramic vehicles. Although the internal factors which influence the mesenchymal stem cells to differentiate into bone as opposed to cartilage cells are not well known, it appears that the direct accessibility of the mesenchymal cells to growth and nutrient factors supplied by the vasculature in porous calcium phosphate ceramics, as opposed to the diffusion chamber, influenced the differentiation of the mesenchymal stem cells to bone.

As a result, the isolated and culturally expanded marrow-derived mesenchymal cells can be utilized under certain specific conditions and/or under the influence of certain factors, to differentiate and produce the desired cell phenotype needed for connective tissue repair or regenerative and/or to the implantation of various prosthetic devices. For example, using porous ceramic cubes filled with culture-expanded human marrow-derived mesenchymal stem cells, bone formation inside the pores of the ceramics has been generated after subcutaneous incubations in immunocompatible hosts. In a recent study conducted by the inventor's lab, i.e. Ohgushi, H., Goldberg, V., and Caplan, A. *Acta Scandia.*, 60:334-339, 1989, rat marrow in a composite graft with porous ceramic was used to fill a segmental defect in the femur of the rat. Bone was shown to fill the pores of the ceramic and anchor the ceramic-marrow graft to the host bone.

The following examples are included for the purposes of further illustrating the detailed steps of the present invention.

EXAMPLE 1

The Isolation, Purification and Cultural Expansion of Marrow-Derived Mesenchymal Cells Marrow Harvest Marrow in femoral head cancellous bone pieces was obtained from patients with degenerative joint disease during hip or knee joint replacement surgery. In addition, marrow was also obtained by iliac aspirate from normal donors and oncology patients who were having marrow harvested for future bone marrow transplantation. All of the oncology patients had malignancies unrelated to the stromal cells and the stromal cells expressed normal karyotype.

Preparation of Marrow for Cell Culture

A. From Plugs of Cancellous Bone Marrow

Plugs of cancellous bone marrow (0.5-1.5 ml) were transferred to sterile tubes to which 25 ml BGJ$_b$ medium (GIBCO, Grand Island, N.Y.) with selected batches of 10% fetal bovine serum (JR Scientific, Woodland, Calif.) (complete medium) was added. The tubes were vortexed to disperse the marrow then spun at 1000×RPM for 5 minutes to pellet cells and bone pieces. The supernatant and fat layer were removed and the marrow and bone were reconstituted in 5 ml complete medium and vortexed to suspend the marrow cells. The suspended cells were collected with a 10 ml syringe fitted with an 16 gauge needle and transferred to separate tubes. Bone pieces were reconstituted in 5 ml. Complete medium and the marrow cells were collected as before. Collection of marrow cells was considered complete when a pellet of yellowish-white cancellous bone pieces was all that remained in the original tube. Marrow cells were separated into a single cell suspension by passing them through syringes filled with 18 and 20 gauge needles. Cells were spun at 1000×g for 5 minutes after which the fat layer and supernatant were removed. Cells were reconstituted in complete medium, counted with a hemocytometer (red blood cells were lyzed prior to counting with 4% acetic acid), and plated in 100 mm dishes at 50–100×10$^6$ nucleated cells/dish.

B. From Aspirate Bone Marrow

Aspirate marrow (5–10 ml) was transferred to sterile tubes to which 20 ml complete medium was added. The tubes were spun at 1000×RPM for 5 minutes to pellet the cells. The supernatant and fat layer were removed and the cell pellets (2.5–5.0 ml) were loaded onto 70% Percoll (Sigma, St. Louis, Mo.) gradients and spun at 460×RPM for 15 minutes. The gradients were separated into three fractions with a pipet: top 25% of the gradient (low density cells-platelet fraction), pooled density=1.03 g/ml; middle 50% of the gradient (high density cells-mononucleated cells), pooled density=1.10 g/ml; and, bottom 25% of the gradient (red blood cells), pooled density=1.14 g/ml. In preliminary experiments each of these three pools were plated separately in complete medium in 100 mm dishes. Adherent cells were observed to be localized to the low density cells. To produce adherent cell cultures for all subsequent experiments only the low density cells were plated.

Culturing and Passaging of Marrow Stromal Cells

Marrow cells from either the femoral head cancellous bone or the iliac aspirate were cultured in complete medium (i.e. BGJ$_b$ medium with 10% fetal bovine serum) at 37° C. in humidified atmosphere containing 95% air and 5% CO$_2$. In preliminary experiments the cells were allowed to attach for 1, 3, or 7 days prior to the initial medium change. No increase in cell attachment was observed after day 1, therefore one day was chosen as the standard length of time at which nonadherent cells were removed from the cultures by replacing the original medium with 7 ml of fresh complete medium. Subsequent medium changes were performed every 4 days. When culture dishes became confluent, the cells were detached with 0.25% trypsin with 0.1 mM EDTA (GIBCO) for 10–15 minutes at 37° C. The action of trypsin was stopped with $\frac{1}{2}$ volume fetal bovine serum. The cells were counted, split 1:3, and replated in 7 ml complete medium. Aliquots of cells were cryopreserved in 90% fetal bovine serum with 10% DMSO (freezing medium).

Preparation of Cultures for In Vivo Incubations in Ceramics and Diffusion Chambers Cultured cells were detached from plates as described for subculturing. After inactivating the trypsin, the cells were washed twice with 10 ml serumless BGJ$_b$ medium, counted, and then adjusted to the appropriate concentration with serumless BGJ$_b$. Whole marrow and Percoll fractions were rinsed twice with 10 ml serumless BGJ$_b$ and adjusted to the appropriate concentration with serumless BGJ$_b$. Porous ceramic cubes (3 mm$^3$) composed of 60% hydroxyapatite+40% β-tricalcium phosphate (Zimmer Corporation, Warsaw, Ind.) were added to the cell suspensions under slight vacuum and soaked for up to 90 minutes prior to surgical implantation.

Diffusion chambers were constructed of lucite rings and Millipore filters as described elsewhere (Ashton, et al., 1980). Cells were prepared as described above and added to the chambers in 100–140 ul of serumless BGJ$_b$ medium. Chambers were sealed with a drop of cement and immersed in serumless BGJ$_b$ for up to 90 minutes prior to surgical implantation.

Surgical Implantation of Ceramics and Diffusion Chambers

Ceramics-Nude mice (National Institute of Health, nu/nu strain) were anesthetized with ether and placed on their stomachs. Four small longitudinal incisions (5 mm) were made along the backs. Ceramic-marrow grafts were inserted into the pockets and positioned as lateral in the pockets as possible. Incisions were closed with Autoclips (Becton Dickenson and Company, Parsippany, N.J.). Each pair of pockets received a different pair of ceramic-marrow graft so that four different samples (2 ceramic cubes per sample) were incubated per mouse.

Diffusion Chambers-Nude mice were anesthetized with ether and placed on their backs. Incisions were made through the skin and peritoneum, and diffusion chambers were inserted into the peritoneal cavity. The peritonea were closed with sutures and the skin, with Autoclips. Only one chamber was inserted per mouse and it contained cultured cells identical to cells loaded in one of the four pairs of the ceramic-marrow grafts implanted into the same mouse.

Histological Evaluation

Nude mice were sacrificed and the ceramic-marrow grafts harvested 1-8 weeks after implantation (Table 1 and Table 3). Ceramic were fixed in 10% buffered formalin, demineralized for 7 hours in RDO Rapid Bone Decalcifier (Dupage Kinetics Laboratories, Inc., Plainfield, Ill.), embedded in paraffin, serial sectioned (5 um thick), and stained with Mallory Heidenhain or Toluidine blue.

Diffusion chambers were harvested 3-10 weeks after implantation (Table 2 and Table 3). Chambers were fixed in 10% buffered formalin, paraffin embedded, serially sectioned, and stained with Mallory Heidenhain or Toluidine blue.

TABLE 2-continued

Incubation of Cultured Human Marrow Cells in Diffusion Chambers

| Donor | Age/Sex | Site | Pass # | Cells/Chamber | 3 | 6 | 8 | 10 |
|---|---|---|---|---|---|---|---|---|
| 5 | 64/M | FH | P | $4.5 \times 10^6$ | — | | | |

P = primary culture
Pass # = the number of subcultures
Site = the site of marrow harvest
FH = femoral head
IC = iliac crest
− = no bone in chamber
+ = 0-30% of chamber contains bone
++ = 30-70% of chamber contains bone
+++ = more than 70% of chamber contains bone

RESULTS

In Vitro Cultures

Adherent marrow-derived mesenchymal cells from femoral head cancellous bone or iliac aspirate have similar morphology, almost all being fibroblastic, with few adipocytic, polygonal or round cells (FIG. 1). Histochemical staining for alkaline phosphatase yields variable positive reactivity with no noticeable difference between cells derived from cancellous bone marrow or aspirate marrow. Adherent cells from both harvest sites fail to produce an extracellular matrix which stains metchromatically with Toluidine blue or positive for von Kossa; a positive staining would have indicated the possibility that cartilage or bone tissue was produced in

TABLE 1

Incubation of Composite Graphs of Cultured Human Marrow Cells and Ceramic in Nude Mouse

| | | | | | Weeks Postimplantation | | | | | | | |
|---|---|---|---|---|---|---|---|---|---|---|---|---|
| Donor # | Age/Sex | Site | Pass # | Conc. | 1 | 2 | 3 | 4 | 5 | 6 | 7 | 8 |
| 1 | 50/M | FH | 4 | $20 \times 10^6$ | | | | | | + | | |
| 1 | 50/M | FH | 5 | $2 \times 10^6$ | | | − | | + | + | | |
| 1 | 50/M | FH | 6 | $0.7 \times 10^6$ | | | + | + | | | | + |
| 2 | 65/M | FH | 1 | $5 \times 10^6$ | | | | | ++ | +++ | | |
| 2 | 65/M | FH | 2 | $4 \times 10^6$ | | | +++ | | | +++ | | +++ |
| 3 | 65/M | FH | P | $6 \times 10^6$ | − | + | | | | +++ | +++ | +++ |
| 4 | 66/F | FH | 1 | $10 \times 10^6$ | | | | + | +++ | +++ | | +++ |
| 5 | 64/M | FH | P | $8 \times 10^6$ | − | + | ++ | | | +++ | | +++ |
| 6 | 64/M | FH | 1 | $4 \times 10^6$ | | | + | | | +++ | | +++ |
| 7 | 67/F | FH | P | $7 \times 10^6$ | − | + | ++ | +++ | | | | |
| 8 | 34/F | IC | 1 | $4 \times 10^6$ | | | − | | | + | | |
| 9 | 42/M | IC | P | $4 \times 10^6$ | | | − | | | − | | |
| 10 | 38/M | IC | P | $4 \times 10^6$ | | | − | | | ++ | | |
| 11 | 45/M | IC | P | $4 \times 10^6$ | | | + | | | ++ | | |

Pass # is the number of subcultures
Conc. is the concentration of cells in cells/ml
Site is the site of marrow harvest
FH - femoral head
IC - Iliac crest
P - primary cultures
− = None of the pores contained bone
+ = 0-30% of the pores contained bone
++ = 30-70% of the pores contained bone
+++ = greater than 70% of the pores contained bone

TABLE 2

Incubation of Cultured Human Marrow Cells in Diffusion Chambers

| Donor | Age/Sex | Site | Pass # | Cells/Chamber | 3 | 6 | 8 | 10 |
|---|---|---|---|---|---|---|---|---|
| 1 | 50/M | FH | 4 | $4 \times 10^6$ | — | | | |
| 2 | 65/M | FH | 1 | $3 \times 10^6$ | — | | | |
| 3 | 65/F | FH | P | $4 \times 10^6$ | — | — | | |
| 4 | 66/F | FH | 1 | $4 \times 10^6$ | — | | | — | these cultures.

In Vivo Incubation of Cultured Marrow Cells with Ceramics

Calcium phosphate ceramic blocks were soaked in culture medium containing various concentrations of cultured marrow-derived mesenchymal cells from either femoral head cancellous bone or iliac aspirate. The marrow donors included both males and females ranging in age from 34 to 67 years old (Table 1). Cells from primary culture and first through sixth passage were assayed, with the cell-loading concentration ranging from $0.7 \times 10^6$ to $20 \times 10^6$ cells/ml. Marrow-derived mesenchymal cell-loaded ceramic blocks were surgically implanted subcutaneously into nude mice and incubated from 1 to 8 weeks. Upon harvest, ceramics were fixed, demineralized and the presence of bone and cartilage was determined by histological evaluation. Table 1 summarizes the data.

Figure 2A:
FIG. 2A shows the formation of new bone (b) lining the pores of the ceramic ghost (c) (40×)
Figure 2B:
FIG. 2B indicates that the fibrous tissue (f) was present in most of the pores (100× of boxed area in FIG. 2A)
Figure 2C:
FIG. 2C indicates that the osteocytes (o) were clearly visible embedded within the bone matrix (400× of boxed area in FIG. 2B)
Figure 3B:
FIG. 3B demonstrates that the fibrous tissue (f) still remained in the inner spaces of most of the pores. In addition, host vascular (v) was also present in some pores (100× of boxed area in FIG. 3A)
Figure 3A:
FIG. 3A indicates that bone (b) was observed lining a greater number of pores of the ceramic ghost (c) than in FIG. 2 (2 week incubation) (40×)
Figure 4B:
FIG. 4B shows the fibrous tissue (f) observed in the inner spaces of a few pores, however, marrow (m) has replaced the fibrous tissue in a majority of the pores (100× of the boxed area in FIG. 4A).
Figure 4A:
FIG. 4A indicates that bone (b) was observed lining most of the pores of the ceramic ghost (c) (40×)

Bone, but not cartilage, was observed in the pores of each graft of ceramics and cultured marrow-derived mesenchymal cells from femoral head cancellous bone. The earliest bone was observed at 2 weeks in less than 30% of the pores of each ceramic (FIG. 2). At three weeks, the number of pores containing bone varied from less than 30% to greater than 70% (FIG. 3). By six weeks, the majority of the ceramics contained bone in greater than 70% of the pores (FIG. 4). No obvious correlation could be made between the age of the donors and the amount of bone formation. In contrast, passage number appeared to have some influence on the amount of bone formation, with primary cultures and early passaged cells (1st-2nd passages) giving more bone formation than late passaged cells (4th-6th passages). Bone formation appears to begin with osteoblast differentiation and bone deposition onto the surfaces of the ceramic pores and appears to progress towards the center of the pores as cells lining the surface of the new bone matrix secrete osteoid on top of previously deposited matrix. Maintenance of ceramic marrow-derived mesenchymal cell grafts for periods of 6-8 weeks resulted in bone remodeling and the identification of marrow elements in the inner spaces of each pore (FIG. 2C).

Grafts of ceramics and cultured marrow-derived mesenchymal cells from iliac aspirate produced bone in three of the four samples tested (Table 1). Cartilage was not observed in any of the grafts. Bone formation in the three positive grafts was less than that observed from ceramics grafted with cultured cells from femoral head cancellous bone marrow. Less than 30% of the pores contained bone at 3 weeks and 30-70% of the pores contained bone at 6 weeks. The remainder of the pores contained fibrous tissue and vasculature of, in all likelihood, host origin.

In Vivo Incubation of Cultured Marrow Cells in Diffusion Chambers

The osteo-chondrogenic potential of cultured marrow-derived mesenchymal cells was also assayed by loading cells in diffusion chambers and surgically implanting them intraperitonelly into nude mice. The cells were obtained from the same cultures used in the ceramic assays (Table 2), and the diffusion chambers were implanted into the peritonea of the same nude mice which received subcutaneous ceramic-marrow-derived mesenchymal cell grafts. After incubations for 3-10 weeks, the chambers were harvested and the presence of bone and cartilage formation determined by histological evaluation. In contrast to the presence of bone in grafts of ceramic and cultured cells from cancellous bone, no bone or cartilage was observed in any of the diffusion chambers containing cultured cancellous bone marrow-derived mesenchymal cells even after 10 weeks incubation (Table 2). Cultured iliac aspirate marrow-derived mesenchymal cells also failed to produce bone or cartilage in the diffusion chambers. Instead, hypocellular sparse fibrous tissue was observed in most of the chambers.

Discussion

In this example, human marrow-derived mesenchymal cells were shown to reproducibly exhibit osteogenic potential following their mitotic expansion in culture when assayed in porous calcium phosphate and/or hydroxyapatite ceramics in nude mice. Osteogenesis was not observed when the same cells were incubated in diffusion chambers in the same nude mice. Collectively, these data show that human marrow contains cells, which can be selected and expanded in culture, which have the potential to differentiate into bone when incubated in vivo as a graft in porous calcium phosphate and/or hydroxyapatite ceramics.

The absence of bone formation in diffusion chambers suggests that the ceramics assay may be a more sensitive assay for differentiation of bone from marrow cells. Bab, et al. (Bab, I., Passi-Even, L., Gazit, D., Sekeles, E., Ashton, B. A., Peylan-Ramu, N., Ziv, I., and Ulmansky, M.; Osteogenesis in vivo diffusion chamber cultures of human marrow cells, *Bone and Mineral* 4; 373, 1988) observed bone in four of eight diffusion chambers implanted with human marrow from two child donors, however, these authors failed to observe bone when whole marrow from older donors was incubated in diffusion chambers in nude mice. In addition, Davies (Davies, J. E., Human bone marrow cells synthesize collagen, in diffusion chambers, implanted into the normal rat, *Cell. Biol. Int. Rep.* 11, 2: 125, 1987) did not observe bone formation in diffusion chambers inoculated with fresh marrow from a five year old female, nor was bone formation observed by Ashton, et al. (Ashton, B. A., Cave, F. A., Williamson, M., Sykes, B. C., Couch, M., and Poser, J. W.; Characterization of cells with high alkaline phosphates activity derived from human bone and marrow; preliminary assessment of their osteogenicity, Bone, 5:313-319, 1985) in diffusion chambers inoculated with cultured fibroblasts from composite pieces of bone and marrow from children and young adults.

In the present example, bone formation was not observed in diffusion chambers inoculated with cultured marrow-derived mesenchymal cells from several older donors. However, bone formation was observed in ceramic filled grafts with cultured marrow-derived mesenchymal cells from the same preparations of older donors (34-67 years old) which failed to generate bone in diffusion chambers. The factors which apparently make ceramics a more sensitive vehicle for bone differentiation from marrow-derived mesenchymal cells are unclear, but may involve direct accessibility of the marrow-derived mesenchymal cells to growth and nutrient factors supplied by the vasculature or direct interaction with vascular cells which are limited because of diffusion chamber geometry (Jaroma, H. J., and Rotsila, V. A., Effect of diffusion chamber pore size on differentiation and proliferation of periosteal cells, *Clin. Orthop.*, 236, 258, 1988) (Villanueva, J. E., and Nimni, M. E., Promotion of calvarial cell osteogenesis by endothelial cells in diffusion chambers, *J. Cell. Biol.*, 109, 4, part. 2.42a (abstract).

The question of origin of the bone formed in the ceramic pores is important since the donor marrow-derived mesenchymal cells are not physically separated from the host cells as is the case for diffusion chambers. Recent data by Goshima, et al. (Jun Goshima, Victor M. Goldberg and Arnold I. Caplan, "The Origin of Bone Formed in Composite Grafts of Porous Calcium Phosphate Ceramic and Marrow Cells" (1989) Submitted) indicate that bone formation in ceramic grafts is a biphasic phenomenon with the initial bone formation being of donor origin. When this donor-derived bone has partially filled the pores of the ceramics, host-derived cells begin remodeling the donor bone, thus beginning the second phase of host-derived bone formation. Eventually, a marrow cavity forms in the center, with a cocoon of host-derived bone which has been laid on the partially remodeled inner surfaces of original donor bone. To confirm the origin of the bone formed with human marrow, the present inventors are currently assaying ceramic grafts with species-specific monoclonal antibodies directed against human osteocytes. The preliminary data shows antibody reactivity to the osteocytes within the grafts, thus suggesting that the bone formed in the porous ceramic is of human and not mouse origin.

Cultured marrow-derived mesenchymal cells originating from femoral head cancellous bone appear to be more osteogenic than cultured marrow-derived mesenchymal cells from iliac aspirated marrow; 9 out of 9 cancellous bone marrow samples produced bone in ceramics, whereas, 3 out of 4 aspirated marrow-derived mesenchymal cell samples produced bone in ceramics. In addition, bone was present in fewer pores in ceramics grafted with aspirated marrow-derived mesenchymal cell than ceramics grafted with femoral head marrow-derived mesenchymal cells. The reasons for the differences is unclear, but, may be associated with the proximity of the harvested marrow stromal cells to the bone surface in the original tissue. Ashton, et al. (Ashton, B. A., Eaglesom, C. C., Bab, I., and Owen, M. E., Distribution of fibroblastic colony-forming cells in rabbit bone marrow and assay of their osteogenic potential by an in vivo diffusion chamber method, *Calcif. Tissue Int.,* 36:83, 1984) showed that cultured rabbit marrow stromal cells differ in their colony forming potential in vitro and osteogenic potential in diffusion chambers depending on their original proximity to the endosteal surface. Cells closest to the endosteal surface were shown to have four times the colony forming efficiency as compared to cells of the core. In the present study, marrow from cancellous bone was harvested by vigorous vortexing to separate the cancellous bone from the marrow cells. This likely produces a population of marrow enriched in cells derived from near the endosteal surface, as compared to aspirate marrow where vigorous separation of marrow cells from cancellous bone is not possible. The inventors observed a consistently higher initial number of adherent cells from cancellous bone marrow as compared to aspirate marrow, which is similar to the observations of Ashton, et al. (Ashton, B. A., Eaglesom, C. C., Bab, I., and Owen, M. E., Distribution of fibroblastic colony-forming cells in rabbit bone marrow and assay of their osteogenic potential by an in vivo diffusion chamber method, *Calcif. Tissue Int.,* 36:83, 1984).

In the case of marrow from adult donors, cartilage was not observed in this study or the study by Bab, et al. (Bab, I., Passi-Even, L., Gazit, D., Sekeles, E., Ashton, B. A., Peylan-Ramu, N., Ziv, I., and Ulmansky, M.; Osteogenesis in in vivo diffusion chamber cultures of human marrow cells, *Bone and Mineral* 4; 373, 1988). It may be that there is an age-dependent determination of marrow-derived cells for the osteogenic lineage over the chondrogenic lineage. Alternatively, culturing conditions in the present study may be selective for osteoprogenitor cells over mesenchymal stem cells or may drive mesenchymal stem cells towards the osteogenic lineage prior to in vivo analysis in ceramics. Present studies are being directed towards addressing these possibilities.

The most important realization from the studies set forth in the above example is that the ceramics graft technique provides a sensitive assay for identifying the osteogenic potential of marrow-derived mesenchymal cells. Importantly, such osteogenic cells can be obtained from human donors of a wide age range. These observations indicate that the ex vivo expansion of cells possessing an osteogenic potential may be used for clinical circumstances requiring augmentation of osteogenesis.

EXAMPLE 2

A. Cellular Repair of Skeletal Defects

The culturally expanded marrow-derived mesenchymal cells can also be used to repair skeletal defects which normally do not heal. One class of skeletal defects that can be repaired, is the class of large skeletal defects in bone caused by injury or produced by the removal of large sections of bone infected with tumor. Under normal circumstances, this type of defect does not heal and creates nonunion of the bone. This type of defect may be treated by implanting cultured mesenchymal cells contained in calcium phosphate and/or hydroxyapatite ceramic vehicles into the defect site. The ceramic will then be osteoconductive to surrounding bone, thereby promoting bony ingrowth along the edges of the ceramic, which will also result in stabilization of the implant in the defect. In addition, the marrow-derived mesenchymal cells will differentiate into osteoblasts, which will then synthesize bone in the ceramic pores. After the cultured cells fill about one third of the pores of the ceramic with bone, applicants expect that the host cells brought in by the vasculature will continue to make bone in the ceramics. Other host cells brought in by the vasculature will then begin to remodel the newly synthesized bone and the ceramic vehicle. Eventually, the defect will become filled with live bone with a marrow cavity in the middle, with the ceramic vehicle becoming completely degraded over time.

A second class of defect that can be repaired by the culture-expanded marrow-derived mesenchymal cells of the present invention, is the damaged articular cartilage generated by trauma or by diseases such as osteoarthritis and rheumatoid arthritis. Under normal circumstances, damage to articular cartilage does not heal, except in very young individuals where the underlying bone is also damaged so that a bloody wound is created. It is projected by the present invention that this type of defect can be treated by implanting cultured marrow-derived mesenchymal cells into the defect. The cells will be formatted in carriers which will hold the cells in the defect, and present them in a manner (round cell morphology) that they differentiate into chondrocytes. In this regard, the applicants envision that a suitable carrier can be constructed of collagen or fibrin, since both have low antiginicity, are pliable to mold to the shape of the defect, and promote round cell shape (which applicants known to be important to induction of chondrocyte differentiation).

B. Stimulation of Hemopoietic Cell Reservoir

From the procedures described in detail in Example 1, implantation of cultured mesenchymal cells in ceramic blocks results in bone formation inside the pores of the ceramic, followed by establishment of a marrow cavity inside the newly layed bone. The cells that generate the marrow cavity must be supplied by the vasculature of the host, which quickly invades the pores of ceramic blocks within a few hours of being implanted.

It is not clearly understood why composite grafts of culture mesenchymal cells and ceramics induce recruitment of hemopoietic stem cells and other marrow elements, however, the fact that this does occur allows for the use of these grafts as a way to sequester hemopoietic stem cells and generate a hemopoietic stem cell reservoir. The reservoir of hemopoietic stem cells can then be used in clinical applications such as marrow transplantation as an alternative method for harvesting hemopoietic stem cells.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method for inducing human marrow-derived mesenchymal stem cells to differentiate into bone-forming cells, comprising:
   a) providing human marrow-derived mesenchymal stem cells that have been isolated, purified and culturally expanded from a bone marrow specimen by adding the bone marrow specimen to a medium which contains factors which stimulate mesenchymal cell growth without differentiation and allows, when cultured, for selective adherence of only the mesenchymal stem cells to a substrate surface;
   b) applying the isolated, purified and culturally expanded human marrow-derived mesenchymal stem cells to a porous carrier; and,
   c) implanting the porous carrier containing the culturally expanded human marrow-derived mesenchymal stem cells into an environment containing factors necessary for differentiating the human mesenchymal stem cells into bone cells.

2. The method of claim 1, wherein said environment is in vivo.

3. The method of claim 1, wherein said porous carrier comprises about 60% hydroxyapatite and about 40% tricalcium phosphate.

4. A method for repairing skeletal defects comprising:
   a) providing marrow-derived human mesenchymal stem cells that have been culturally expanded from isolated and purified human marrow-derived mesenchymal stem cells which have been isolated from a bone marrow specimen by adding the bone marrow specimen to a medium which contains factors which stimulate mesenchymal cell growth without differentiation and allows, when cultured, for selective adherence of only the mesenchymal stem cells to a substrate surface;
   b) applying the culturally expanded marrow-derived human mesenchymal stem cells to a porous carrier; and,
   c) implanting the porous carrier containing the culturally expanded purified human marrow-derived mesenchymal stem cells into the defective skeletal tissue.

5. The method of claim 4, wherein said porous carrier is comprised of about 60% hydroxyapatite and about 40% tricalcium phosphate.

6. A method for repairing skeletal defects comprising:
   a) providing a bone marrow specimen containing human marrow-derived mesenchymal stem cells and bone pieces;
   b) adding the bone marrow specimen to a medium thereby producing a bone marrow specimen-medium mixture, wherein said medium contains factors which stimulate human marrow-derived mesenchymal stem cell growth without differentiation and allows, when cultured, for selective adherence of only the human marrow-derived mesenchymal stem cells to a substrate surface;
   c) separating the bone pieces from the bone marrow medium mixture;
   d) dissociating marrow cells in the bone marrow specimen-medium mixture into single cells;
   e) culturing the dissociated marrow cells in the bone marrow specimen-medium mixture thereby selectively adhering only the human mesenchymal stem cells to the substrate surface;
   f) separating non-adherent matter from the substrate surface, thereby producing isolated culturally expanded human mesenchymal stem cells;
   g) removing remaining adherent isolated and culturally expanded human mesenchymal stem cells from the substrate surface with a releasing agent;
   h) applying the isolated and culturally expanded human marrow-derived mesenchymal stem cells to a porous carrier comprised of about 60% hydroxyapatite and about 40% tricalcium phosphate; and,
   i) implanting the porous carrier containing the culturally expanded human marrow-derived mesenchymal stem cells into the defective skeletal tissue.

7. The method of claim 6, wherein said porous carrier is comprised of about 60% hydroxyapatite and about 40% tricalcium phosphate.

8. The method of claim 6, wherein said medium is comprised of BGJ$_b$ Medium with 10% fetal bovine serum.

9. The method of claim 6, wherein said medium is comprised of F-12 Nutrient Mixture.

10. A method for inducing marrow-derived human mesenchymal stem cells to differentiate into cartilage-forming cells, comprising:
   a) providing human marrow-derived mesenchymal stem cells that have been culturally expanded from isolated and purified human marrow-derived mesenchymal stem cells which have been isolated from a bone marrow specimen by adding the bone marrow specimen to a medium which contains factors which stimulate mesenchymal cell growth without differentiation and allows, when cultured, for selective adherence of only the mesenchymal stem cells to a substrate surface;
   b) applying the culturally expanded human marrow-derived mesenchymal stem cells to a carrier formatted to promote round cell morphology;
   c) implanting the carrier containing the culturally expanded human marrow-derived mesenchymal stem cells into an environment containing factors necessary for differentiating the human mesenchymal stem cells into cartilage-forming cells.

11. A method for repairing damaged articular cartilage comprising:
   a) providing human marrow-derived mesenchymal stem cells that have been culturally expanded from isolated and purified human marrow-derived mesenchymal stem cells which have been isolated from a bone marrow specimen by adding the bone marrow specimen to a medium which contains factors which stimulate mesenchymal cell growth without differentiation and allows, when cultured, for selective adherence of only the mesenchymal stem cells to a substrate surface;

b) applying the culturally expanded human marrow-derived mesenchymal stem cells to a carrier formatted to promote round cell morphology; and, c) implanting the carrier containing the culturally expanded human marrow-derived mesenchymal stem cells into the damaged articular cartilage.

12. A method for repairing damaged articular cartilage comprising:

a) providing a bone marrow specimen containing human mesenchymal stem cells and bone pieces;

b) adding the bone marrow specimen to a medium thereby producing a bone marrow specimen-medium mixture, wherein said medium contains factors which stimulate human marrow-derived mesenchymal stem cell growth without differentiation and allows, when cultured, for selective adherence of only the human marrow-derived mesenchymal stem cells to a substrate surface;

c) separating the bone pieces from the bone marrow specimen-medium mixture;

d) dissociating marrow cells in the bone marrow specimen-medium mixture into single cells;

e) culturing the dissociated marrow cells in the bone marrow medium specimen-mixture thereby selectively adhering only the human mesenchymal stem cells to the substrate surface;

f) separating non-adherent matter from the substrate surface, thereby producing isolated culturally expanded human marrow-derived mesenchymal stem cells;

g) removing remaining adherent isolated culturally expanded human mesenchymal stem cells from the substrate surface with a releasing agent;

h) applying the isolated culturally expanded human marrow-derived mesenchymal cells to a carrier formatted to promote round cell morphology; and, i) implanting the carrier containing the culturally expanded human marrow-derived mesenchymal cells into the damaged articular cartilage.

13. The method of claim 12, wherein said medium is comprised of $BGJ_b$ Medium with 10% fetal bovine serum.

14. The method of claim 12, wherein said medium is comprised of F-12 Nutrient Mixture.

15. A method for repairing skeletal defects comprising:

a) providing a bone marrow specimen containing human mesenchymal stem cells;

b) adding the bone marrow specimen to a medium thereby producing a bone marrow specimen-medium mixture, wherein said medium contains factors that stimulate mesenchymal stem cell growth without differentiation and allows, when cultured, for selective adherence of only the mesenchymal stem cells to a substrate surface;

c) adding the bone marrow specimen-medium mixture to a density gradient which separates cells into low, medium and high density cell fractions based on differences in density;

d) removing the low density cell fraction from the density gradient;

e) adding the low density cell fraction to the medium used in step (b) to produce a low density cell fraction-medium mixture;

f) culturing the low density cell fraction-medium mixture, thereby selectively adhering only the mesenchymal stem cells to the substrate surface;

g) removing any non-adherent matter from the substrate surface;

h) removing remaining adherent mesenchymal stem cells from the substrate surface with a releasing agent, thereby allowing for the isolated mesenchymal stem cells to be recovered;

i) applying the recovered isolated mesenchymal stem cells to a porous carrier comprised of about 60% hydroxyapatite and about 40% tricalcium phosphate; and, j) implanting the porous carrier containing the culturally expanded human marrow-derived mesenchymal stem cells into the skeletal defect.

* * * * *

UNITED STATES PATENT AND TRADEMARK OFFICE
CERTIFICATE OF CORRECTION

PATENT NO. : 5,197,985
DATED : March 30, 1993
INVENTOR(S) : Caplan, et al.

It is certified that error appears in the above-indentified patent and that said Letters Patent is hereby corrected as shown below:

Column 1, between lines 6 and 7 before first full paragraph insert

-- the United States Government has rights in this invention pursuant to a Grant DE 04008 awarded by National Institutes of Health, to Case Western Reserve University. --

Signed and Sealed this

Tenth Day of May, 1994

*Attest:*

BRUCE LEHMAN

*Attesting Officer*     *Commissioner of Patents and Trademarks*